(12) United States Patent
Solomon

(10) Patent No.: US 10,850,069 B2
(45) Date of Patent: Dec. 1, 2020

(54) METHODS AND DEVICES FOR VASCULAR ACCESS

(71) Applicant: I-V Access Technology, Inc., Los Osos, CA (US)

(72) Inventor: Clint Solomon, Morgan Hill, CA (US)

(73) Assignee: I-V Access Technology, Inc., Los Osos, CA (US)

(*) Notice: Subject to any disclaimer, the term of this patent is extended or adjusted under 35 U.S.C. 154(b) by 0 days.

(21) Appl. No.: 16/670,291

(22) Filed: Oct. 31, 2019

(65) Prior Publication Data

US 2020/0061346 A1 Feb. 27, 2020

Related U.S. Application Data

(63) Continuation of application No. 16/520,813, filed on Jul. 24, 2019, which is a continuation of application No. 16/004,970, filed on Jun. 11, 2018, now Pat. No. 10,406,326.

(60) Provisional application No. 62/552,663, filed on Aug. 31, 2017.

(51) Int. Cl.
| | |
|---|---|
| *A61M 25/06* | (2006.01) |
| *A61M 39/10* | (2006.01) |
| *A61M 39/26* | (2006.01) |
| *A61M 25/00* | (2006.01) |
| *A61M 29/00* | (2006.01) |

(52) U.S. Cl.
CPC .... *A61M 25/0606* (2013.01); *A61M 25/0625* (2013.01); *A61M 39/1011* (2013.01); *A61M 25/0097* (2013.01); *A61M 25/0631* (2013.01); *A61M 29/00* (2013.01); *A61M 39/26* (2013.01); *A61M 2025/0687* (2013.01)

(58) Field of Classification Search
CPC .............. A61M 39/1011; A61M 39/26; A61M 2025/0606; A61M 25/0625; A61M 25/0097; A61M 25/0631; A61M 2025/0687; A61M 29/00
See application file for complete search history.

(56) References Cited

U.S. PATENT DOCUMENTS

| | | |
|---|---|---|
| 3,195,786 A | 7/1965 | Vogt |
| 3,347,232 A | 10/1967 | Abraham |
| 3,861,416 A | 1/1975 | Wichterle |
| 4,341,239 A | 7/1982 | Atkinson |
| 4,465,102 A | 8/1984 | Rupp |

(Continued)

FOREIGN PATENT DOCUMENTS

| | | |
|---|---|---|
| EP | 1291035 | 3/2003 |
| FR | 2655859 | 6/1991 |

(Continued)

*Primary Examiner* — Theodore J Stigell
(74) *Attorney, Agent, or Firm* — Levine Bagade Han LLP

(57) ABSTRACT

Methods and devices to facilitate positioning of a catheter into a vessel. Devices include axially concentric assemblies of a piercing needle and a dilator that guides an outer catheter into a vessel, such as a blood vessel. The assemblies described herein can include retraction mechanisms and/or lock mechanisms to control needle positioning during catheterization processes as well as improved valves that prevent leakage of fluid from the proximal end of the devices. The devices and method include the use of novel valves to prevent undesired leakage of fluids through the proximal end of the catheter.

10 Claims, 12 Drawing Sheets

(56) References Cited

U.S. PATENT DOCUMENTS

| | | |
|---|---|---|
| 4,524,805 A | 6/1985 | Hoffman |
| 4,565,545 A | 1/1986 | Suzuki |
| 4,588,398 A | 5/1986 | Daugherty et al. |
| 4,629,450 A | 12/1986 | Suzuki et al. |
| 4,655,752 A | 5/1987 | Honkanen et al. |
| 4,758,225 A | 7/1988 | Cox et al. |
| 4,950,257 A | 8/1990 | Hibbs et al. |
| 5,010,925 A | 4/1991 | Atkinson et al. |
| 5,092,857 A | 3/1992 | Fleischhacker |
| 5,114,408 A * | 5/1992 | Fleischhaker ..... A61M 39/0606 604/167.04 |
| 5,122,118 A | 6/1992 | Haber et al. |
| 5,242,410 A | 9/1993 | Melker |
| 5,295,658 A | 3/1994 | Atkinson et al. |
| 5,405,323 A * | 4/1995 | Rogers ............. A61M 39/0693 604/167.04 |
| 5,445,617 A | 8/1995 | Yoon |
| 5,456,284 A | 10/1995 | Ryan et al. |
| 5,527,290 A | 6/1996 | Zadini et al. |
| 5,618,272 A | 4/1997 | Nomura |
| 5,843,046 A | 12/1998 | Motisi et al. |
| 6,035,896 A | 3/2000 | Liardet |
| 6,165,168 A * | 12/2000 | Russo ................ A61M 39/045 604/247 |
| 6,267,748 B1 | 7/2001 | Gulliksen et al. |
| 6,607,511 B2 | 8/2003 | Halseth et al. |
| 6,702,255 B2 | 3/2004 | Dehdashtian |
| 6,706,017 B1 | 3/2004 | Dulguerov |
| 7,736,339 B2 | 6/2010 | Woehr et al. |
| 7,753,338 B2 | 7/2010 | Desecki |
| 7,892,209 B2 | 2/2011 | Harand et al. |
| 7,938,805 B2 | 5/2011 | Harding et al. |
| 8,006,953 B2 | 8/2011 | Bennett |
| 8,092,432 B2 * | 1/2012 | Nordgren ............ A61M 39/24 604/247 |
| 8,105,288 B2 | 1/2012 | Keyser et al. |
| 8,469,928 B2 | 6/2013 | Stout et al. |
| 8,591,469 B2 | 11/2013 | Keyser et al. |
| 9,028,425 B2 | 5/2015 | Burkholz |
| 9,114,231 B2 | 8/2015 | Woehr et al. |
| 9,155,863 B2 | 10/2015 | Isaacson et al. |
| 9,155,864 B2 | 10/2015 | Stout et al. |
| 9,604,035 B2 | 3/2017 | Keyser et al. |
| 9,775,973 B2 | 10/2017 | Keyser et al. |
| 10,406,326 B2 | 9/2019 | Solomon |
| 2004/0092879 A1 | 5/2004 | Kraus et al. |
| 2004/0097880 A1 | 5/2004 | Schur |
| 2004/0193109 A1 | 9/2004 | Prestidge et al. |
| 2005/0187524 A1 | 8/2005 | Willis et al. |
| 2005/0256460 A1 | 11/2005 | Rome et al. |
| 2006/0200083 A1 | 9/2006 | Freyman et al. |
| 2007/0250037 A1 | 10/2007 | Brimhall et al. |
| 2007/0282268 A1 | 12/2007 | Mayse |
| 2008/0092571 A1 | 4/2008 | Allison et al. |
| 2008/0093571 A1 | 4/2008 | Desecki |
| 2008/0172003 A1 | 7/2008 | Plishka et al. |
| 2009/0209912 A1 | 8/2009 | Keyser et al. |
| 2009/0209914 A1 | 8/2009 | Koch et al. |
| 2011/0056569 A1 | 3/2011 | Chambo et al. |
| 2012/0150118 A1 | 6/2012 | Keyser et al. |
| 2012/0221024 A1 * | 8/2012 | Sutton .................. A61M 39/06 606/151 |
| 2013/0204226 A1 | 8/2013 | Keyser |
| 2014/0058357 A1 | 2/2014 | Keyser et al. |
| 2015/0265827 A1 | 9/2015 | Keyser et al. |
| 2016/0271370 A1 | 9/2016 | Keyser et al. |
| 2017/0326341 A1 | 11/2017 | Liska |
| 2018/0064912 A1 | 3/2018 | Keyser et al. |
| 2019/0060616 A1 | 2/2019 | Solomon |
| 2020/0016375 A1 | 1/2020 | Solomon |

FOREIGN PATENT DOCUMENTS

| | | |
|---|---|---|
| FR | 2687320 | 8/1993 |
| JP | 07-136285 | 5/1995 |
| JP | 09-047512 | 2/1997 |
| JP | 2007-260218 | 10/2007 |
| JP | 2011-234802 | 11/2011 |
| TW | 368422 | 9/1999 |
| TW | 592741 | 6/2004 |
| WO | WO 1992/016248 | 10/1992 |
| WO | WO 2003/013627 | 2/2003 |
| WO | WO 2009/091514 | 7/2009 |
| WO | WO 2013/119557 | 8/2013 |
| WO | WO 2019/476456 | 3/2019 |

\* cited by examiner

METHODS AND DEVICES FOR VASCULAR ACCESS

CROSS-REFERENCE TO RELATED APPLICATIONS

This application is a continuation of U.S. patent application Ser. No. 16/520,813 filed Jul. 24, 2019, which is a continuation of U.S. patent application Ser. No. 16/004,970 filed Jun. 11, 2018 (now U.S. Pat. No. 10,406,326), which claims priority to U.S. Provisional Patent Application No. 62/552,663 filed Aug. 31, 2017, the contents each of which are incorporated herein by reference in their entirety.

FIELD OF THE INVENTION

The invention is directed to methods and devices to facilitate positioning of a catheter into a vessel. Devices include axially concentric assemblies of a piercing needle and a dilator that guides an outer catheter into a vessel, such as a blood vessel. The assemblies described herein can include retraction mechanisms and/or lock mechanisms to control needle positioning during catheterization processes as well as improved valves that prevent leakage of fluid from the proximal end of the devices.

BACKGROUND

Intravenous venous catheterization involves the insertion of a small catheter into a peripheral blood vessel, typically for the administration of medication, fluids or drawing of blood. The act of inserting an intravenous catheter presents risks to both healthcare workers and patients. For example, healthcare workers face a risk of infection upon being exposed to a patient's bodily fluids. In addition, when the healthcare worker removes a needle used during catheterization of the patient, the healthcare worker must take significant care to prevent the sharp needle from inadvertently penetrating the skin of the healthcare worker.

Another concern involves the patient. Namely, to successfully access veins, even small, fragile or traumatically stressed ones, there is a desire to minimize the trauma and minimize the size of the introducer needle. This concern is balanced against the need for the needle to allow for introduction of a catheter over the needle and into the vessel.

Once the catheter is properly inserted, it is important to minimize fluid or blood leakage from the proximal end of the catheter while a connector is coupled to the inserted catheter.

The devices, methods and systems described herein provide for an improved catheter and/or needle assembly.

SUMMARY

The illustrations and variations described herein are meant to provide examples of the methods and devices of the invention. It is contemplated that combinations of aspects of specific embodiments or combinations of the specific embodiments themselves are within the scope of this disclosure.

The methods, devices, and systems described herein provides several benefits over conventional needle systems. For example, the needle assemblies described herein allow for insertion of the catheter using a small gauge needle by incorporating a dilator to expand the passage into the vessel allowing for an easy introduction of the catheter into the vein or other body target. The use of a smaller needle and dilator can reduce pain and/or anxiety of the patient as well as reduce the risk of vascular damage. The systems described herein also permit a fully passive or active needle retraction to withdraw the needle tip safely within the dilator or other member. This retraction method allows for positioning of the catheter in the vein with less risk of vascular damage that could otherwise lead to hematoma or infiltration.

In addition, the catheters described herein can employ a one way, blood control valve that reduces the risk of blood leakage, until catheter is fluidly coupled to a separate line.

In addition, the needle assembly described herein includes an improved needle assembly. For example, such a needle assembly can include a housing having a projection located therein; a first tubular member having a first hub slidably engaged with the housing; a needle having a needle hub, the needle extending through the first tubular member, the needle hub positioned within the assembly housing, the needle hub including a stop material positioned in a fluid path of the needle hub such that fluids passing through the needle into the needle hub contacts the stop material; a biasing element in contact with the needle hub applying a biasing force against the needle hub; where the needle assembly comprises an unloaded configuration where the stop material and the projection are adjacent without the biasing force acting therebetween; where the first hub and needle hub are moveable relative to each other to assume a loaded configuration where the biasing force drives the needle hub proximally to force the stop material against the projection such that the stop material prevents further proximal movement of the needle hub; and wherein when fluid in the needle hub contacts the stop material, the stop material weakens causing proximal movement of the needle hub such that a distal end of the needle retracts within the first tubular member.

In one variation, the needle assembly, in the unloaded configuration and in the loaded configuration, the distal end of the needle extends beyond a distal end of first tubular member.

The first tubular member can comprise a dilator with a catheter positioned exterior to the dilator. In one variation, the needle assembly is actuatable by rotation of the first hub relative to the needle hub.

The assembly can comprise a first hub having a slotted opening and where the needle hub comprises a protruding element within the slotted opening, where in the unloaded configuration, a surface of the slotted opening prevents rearward movement of the protruding element, and upon rotation of the first hub relative to the needle hub the slotted opening permits proximal movement of the protruding element and the needle hub. In one variation, a portion of the slotted opening is angled to permit gradual proximal movement of the protruding element and the needle hub during rotation of the first hub.

Variations of the device can include a needle assembly where the first hub comprises a locking surface, such that upon rotation of the first hub, a locking arm enters the locking surface to prevent further rotation of the first hub. For example, the assembly can include a protective cap positioned exterior to the first tubular member and the needle.

In variations of the device, in the unloaded configuration, the needle hub can be touching or can be spaced from the projection.

The devices described herein can include one or more slider arms extending exterior to the housing, where the slider arm is moveable from an exterior of the housing such that proximal movement of the slider arm moves the needle hub proximally sufficient to force the projection through the stop material to retract the needle within the first tubular member.

Variations of the housing include an end cap at a proximal end, and where the projection comprising a tapered projection extending distally from the end cap.

The stop material can comprise any structure such as a membrane positioned within a proximal end of the needle hub or over a proximal end of the needle hub. In alternate variations, the stop material comprises a plug positioned in a proximal end of the needle hub.

The needle assembly can include one or more visually transparent or visually translucent sections to permit visual detection of fluid entering or passing through the needle hub.

In another example, the present disclosure includes a medical assembly comprising an assembly housing having a projection located therein; a first tubular member having a first hub coupled with the assembly housing; a needle having a needle hub, the needle extending through the first tubular member, the needle hub positioned within the assembly housing, the needle hub including a positioned in a fluid path of the needle hub such that fluids passing through the needle into the needle hub engage the stop material; where the needle assembly is actuatable from an unloaded configuration to a loaded configuration during which a distal end of the needle extends beyond a distal end of the first tubular member, where in the unloaded configuration a mechanical stress restrains the needle assembly from moving in a proximal direction without increasing mechanical stress on the stop material wherein in the loaded configuration a biasing element moves the needle hub proximally until the stop material engages the projection increases mechanical stress on the stop material, which prevents further proximal movement of the needle hub and; wherein as fluid from the needle hub contacts the stop material, a structural integrity of the stop material reduces eventually permitting proximal movement of the needle hub such that the distal end of the needle retracts within the first tubular member.

The present disclosure also includes methods of preparing an injection into a vessel of an individual and methods of catheterization.

For example, such methods can comprise providing a needle assembly having a needle extending through an outer tubular member, where the needle comprises a stop material coupled to a needle hub, where the needle assembly is in an unloaded configuration such that a mechanical stress of the stop material is at a first level, where the stop material reduces a structural integrity when exposed to fluids; moving the needle hub and a hub of the outer tubular member relative to each other resulting in an increase in the mechanical stress of the stop material to a second level, while a distal end of the needle extends beyond a distal end of the outer tubular member.

Another method includes a method of preparing an injection into a vessel of an individual. For example, the method can comprise providing a needle assembly having a needle extending through an outer tubular member, where the needle comprises a stop material that reduces a structural integrity when exposed to fluids, the stop material being coupled to a needle hub, where the needle assembly is in an unloaded configuration such that such that the needle hub is prevented from proximal movement without increasing mechanical stress on the stop material; moving the needle hub and a hub of the outer tubular member relative to each other such that a bias force forces the needle hub in a proximal direction until the stop material engages a portion of the needle assembly resulting in a state of increased mechanical stress on the stop material, where a distal end of the needle extends beyond a distal end of the outer tubular member when in the stop material is in the state of increased mechanical stress.

Another variation of devices described herein includes catheter assemblies for use with a male luer having a distal end and a lateral surface, the male luer having a connector portion, the catheter assembly comprising: a catheter hub having a chamber with a proximal surface defining an open proximal end; a catheter tubing coupled the catheter hub and having a lumen in fluid communication with the chamber; a septum valve comprising: a barrier layer at a distal end, the barrier layer having at least one slit, a wall portion extending proximally from the barrier layer, the wall portion defining a valve cavity therein, a flange portion at a proximal end of the septum valve, the flange portion having a diameter greater than a diameter of the wall portion; the septum valve is coupled to the catheter hub such that the flange portion engages the proximal surface of the catheter hub exterior to the chamber and the wall portion engages a surface of the chamber; and wherein insertion of the male luer into the cavity of the septum valve causes the distal end of the male luer to open the slit, while the lateral surface of the male luer engages the wall portion within the cavity causing the wall portion to engage an interior surface of the chamber, and where the connector portion engages the flange portion against the proximal surface of the catheter hub.

Variations of the catheter assembly include a catheter assembly positioned about the needle assemblies described herein.

Variations of the catheter assembly of can include a flange portion of a septum valve being affixed to the proximal surface of the catheter hub and where the wall portion of the septum valve contacts the interior surface of the chamber of the catheter hub. The slit in the barrier layer of the septum valve is normally closed and opened upon the application of a force. The slit in the barrier layer of the septum valve comprises a tri-slit that forms three leaflet portions in the barrier layer.

The present disclosure is related to the following commonly assigned patents and applications, the entirety of each of which is incorporated by reference: U.S. application Ser. No. 12/319,715 now U.S. Pat. No. 8,105,288 issued on Jan. 31, 2012; U.S. application Ser. No. 13/331,910 now U.S. Pat. No. 8,591,469 issued on Nov. 26, 2013; U.S. application Ser. No. 15/169,717 now U.S. Pat. No. 9,604,035 issued on Mar. 28, 2017; U.S. application Ser. No. 14/062,124 published as US20140058357 on Feb. 27, 2014; U.S. application Ser. No. 13/759,643 published as US20130204226 on Aug. 8, 2013; and U.S. application Ser. No. 14/660,151 published as US20150265827 on Sep. 24, 2015.

BRIEF DESCRIPTION OF THE DRAWINGS

Each of the following figures diagrammatically illustrates aspects and variation to better understand the invention. Variation of the invention from the aspects shown in the figures is contemplated.

DETAILED DESCRIPTION

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising. (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1A:
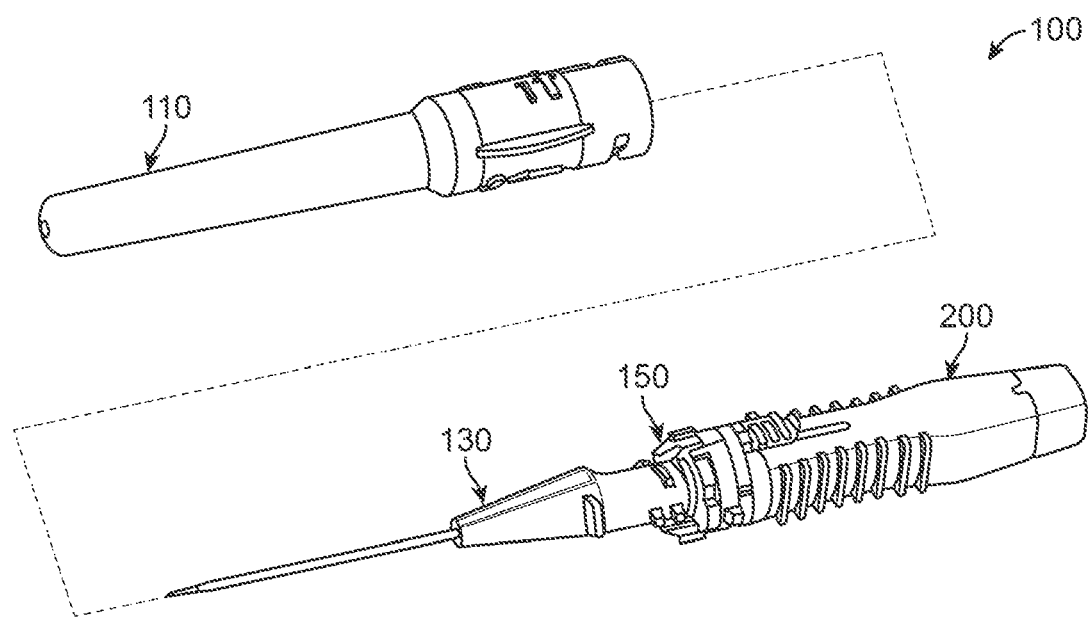
FIG. 1A illustrate an example of an improved needle assembly with a protective cap covering a catheter.

FIG. 1A illustrate an example of an improved needle assembly with a protective cap 110 covering a catheter 130. Where the catheter is coupled to a dilator 150 that is engaged with a housing 200. Any portion of the housing 200 and components positioned therein can include transparent or translucent sections to allow for visual detection of blood or fluid flow therein.

Variations of the devices and methods under the present invention can include needle assemblies that do not include a cap 110 or catheter 130. In addition, alternate embodiments of the methods and devices can include the use of a sheath or other tubular member in place of a dilator 150.

Figure 1B:
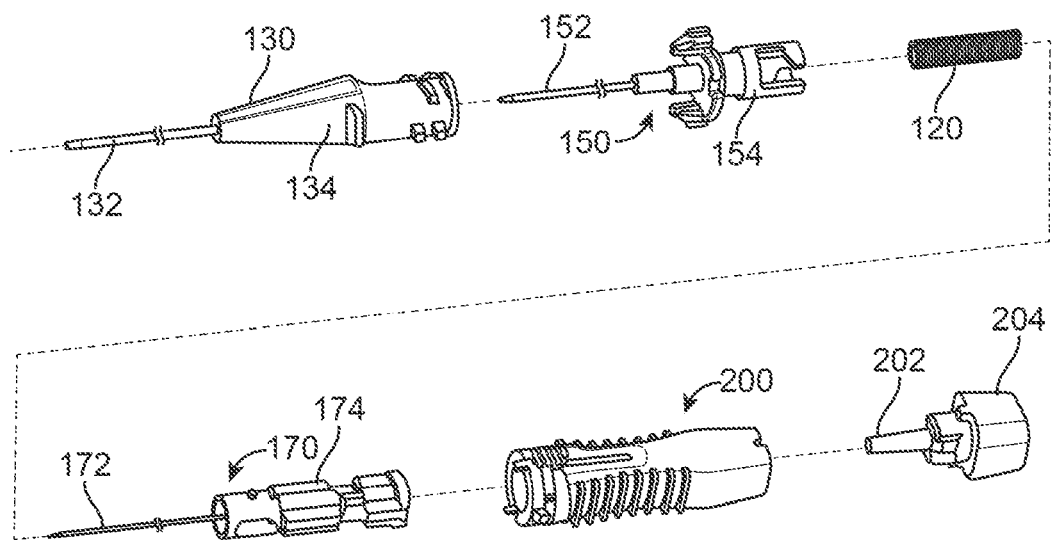
FIG. 1B shows an exploded view of the needle assembly of FIG. 1A.

FIG. 1B shows an exploded view of the needle assembly 100 of FIG. 1A. In this variation, the cap 110 is not shown for purposes of illustrating the assembly. As shown, a catheter 130 comprising a catheter extrusion or tubing 132 and catheter hub is positioned over a dilator 150. The dilator 150 can include a dilator tubing 152 coupled to a dilator hub. Variations of the dilator tubing 152 can be flexible, stiff, or a tubing that has varying properties along its length. The dilator 150 is slidably positioned over a needle 170 comprising a cannula 172 and needle hub 175 with a biasing element 120 positioned between the dilator hub 154 and needle hub 174 to apply a biasing force as described below. The biasing element 120 in the illustrated example comprises a coil spring. However, variations of the device can include any elastic or resilient member that can provide a biasing force. For example, an elastic resin, or other type of spring can be used to provide a biasing force that drives the needle 170 in a proximal direction relative to the dilator 150. The dilator hub 154, biasing element 120, and needle hub 174 can be slidably engaged within a housing 200. As described below, the housing 200 can include a projection stop, projection or punch member 202 that is used to resist rearward movement of the needle 170. The projection 202 is illustrated as being part of an insert 204 that seats in a proximal end of the housing 200. However, variations can include a projection 202 that is integrally formed with the housing. Likewise, the illustrated projection comprises a tapered shape. However, alternate shapes are within the scope of this disclosure.

As described above, the assembly illustrated in FIG. 1B includes a catheter 130 and a dilator 150. However, variations of the invention can include embodiments without a catheter and/or embodiments where a generic tubular member with a hub is used in place of dilator 150.

Figure 2:
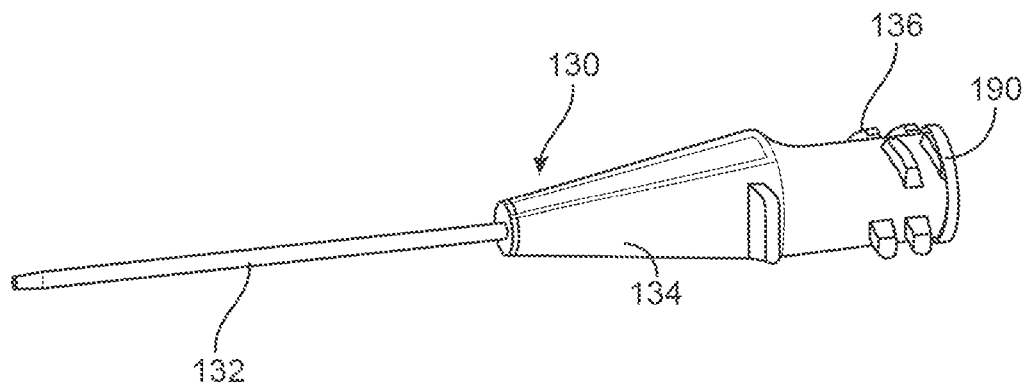
FIG. 2 illustrates a variation of a catheter having an extrusion or tubing coupled to a hub.

As described herein, for variations of the system 100 that use a catheter 130, using a dilator 150 over a needle 170 allows the use of a small needle size as compared to a catheter size. For example, the use of dilator 150 allows for placement of a 20 GA catheter using a 24 GA needle. However, alternate variations of the devices can include catheters of any gauge, where the gauge is selected based on the desired medical procedure. FIG. 2 illustrates a variation of a catheter 130 having an extrusion or tubing 132 coupled to a hub 134. The hub 134 can include any number of features that allow for joining of the catheter 130 with fittings to deliver or remove fluids, medicine, or blood to/from the body. In this variation, the catheter hub 134 includes projections 136 that allow for a threaded engagement of another hub onto the proximal end of the catheter. 130. As shown, variations of the catheter 130 can include an improved septum valve 190 as discussed below.

Figure 3:
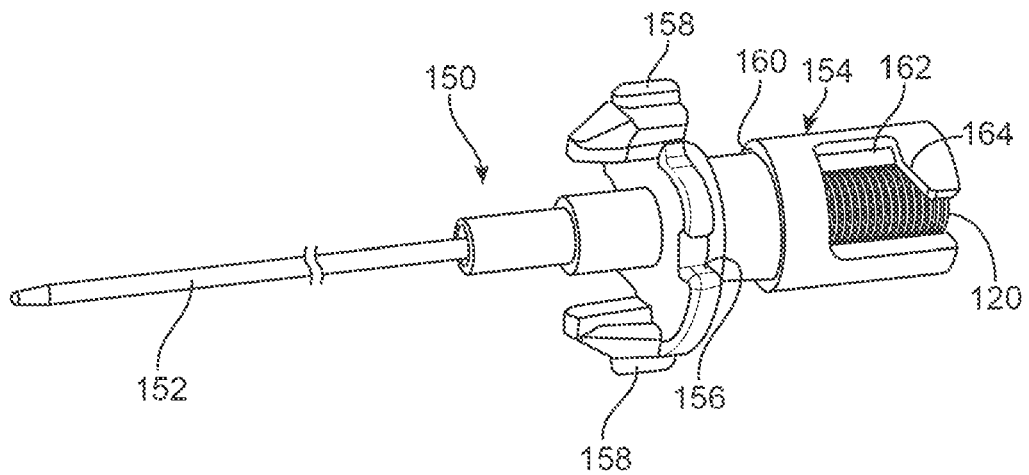
FIG. 3 illustrate an example of a dilator including a dilator tubing coupled to a dilator hub where a biasing element is nested within the dilator hub.

FIG. 3 illustrate an example of a dilator 150 including a dilator tubing 152 coupled to a dilator hub 154 where a biasing element 120 is nested within the dilator hub 154. In alternate variations, a biasing element can be positioned external to the dilator hub. Alternatively, the biasing element can be positioned in another part of the needle assembly 100 as long as it provides a direct or indirect biasing force on the needle to urge the needle in a proximal direction. In the broadest example, a dilator hub 154 can comprise an ordinary hub as commonly used in medical catheters. Alternatively, a variation of a hub (for a dilator or any other tubular member, or generic sheath), can include features to improve the operability of the needle assembly 100. For instance, the illustrated hub 154 can include one or more locking surfaces 156 to prevent rotation of the hub 154 when moved from an unloaded configuration to a loaded configuration as shown below. The hub 154 can also include one or more projections/protrusions/tab features 158 that, when used with a cap 110 (shown in FIG. 1A) provide for alignment and rotation of the hub 154 with the cap. The hub 154 can also optionally include a groove or recess 160 that can be used with one more retaining clips to assist in preventing rotation of the hub 154. FIG. 3 also illustrates a slotted opening 162 that can serve multiple functions. For example, the slotted opening 162 can be used to help prevent rearward movement of the needle/needle hub as well as to permit controlled proximal movement of the needle hub as described below.

Figure 4A:
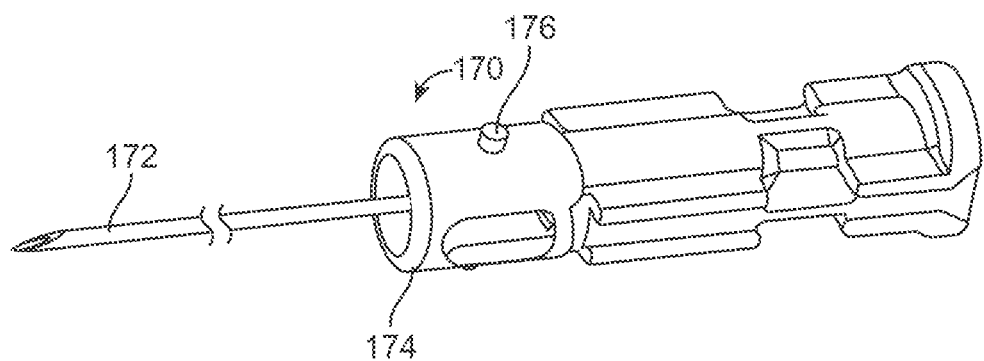
FIGS. 4A and 4B illustrate a side view and cross sectional view of a needle having a needle cannula affixed with a needle hub.
Figure 4B:
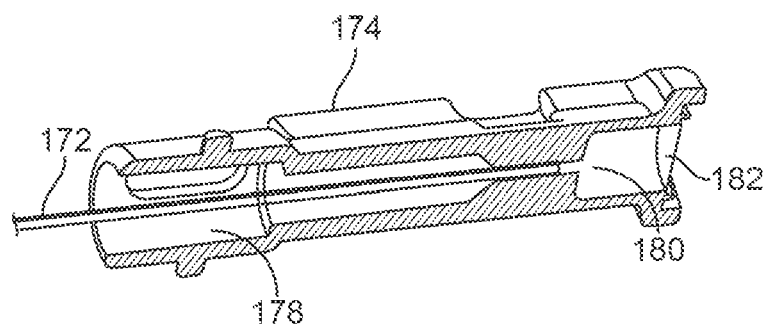

FIGS. 4A and 4B illustrate a side view and cross sectional view of a needle 170 having a needle cannula 172 affixed with a needle hub 174. The needle hub 174 receives a portion of the biasing element (shown in FIG. 3) in a distal portion 178 of the hub 174. However, in alternate variations, the biasing element can engage an exterior portion of the needle as well. The needle hub includes one or more protrusions or catch features 176 that can engage with the slotted opening 162 (shown in FIG. 3) of the dilator hub 154. The needle hub 174 also includes a chamber 180) that is in fluid communication with a lumen of the cannula 172). A stop material 182 is also coupled to the needle hub 174. The stop material 182 can comprise a fluid sensitive material that degrades in structural integrity upon contact with fluid. The stop material 182 can comprise a membrane, thin layer, or plug.

Figure 5:
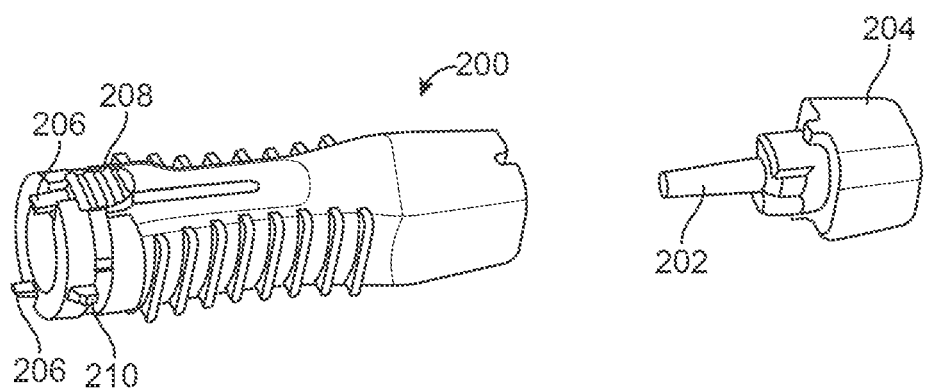
FIG. 5 illustrates a variation of a housing for the needle assembly.

FIG. 5 illustrates a variation of a housing 200 for the needle assembly 100. As shown, the housing 200 can include a projection or punch member 202 that engages the stop material (as discussed below). In the illustrated variation, the projection 202 is formed form an insert 204 that is inserted into a proximal end of the housing 200. However, as noted above, the projection can be integrally formed in the hub. The housing 200 can further include one or more locking features 206 that engage the locking surface (shown in FIG. 3) of the dilator hub. In this variation, the locking features 206 extend from spring clips positioned about the housing 200. In alternate variations, the locking features 206 can be integrally formed with the housing 200. The housing can also optionally include a slider or slider arm 208 that extends exteriorly to the housing 200. The slider 208 includes a portion (not shown) that engages the needle to allow for manual retraction of the needle. Such a feature can serve as an added measure of safety that the medical practitioner can check to ensure full retraction of the needle. The housing 200 can also include one or more alignment features 210 that require alignment of the cap with the feature 210 prior to removal of the cap.

Figure 6A:
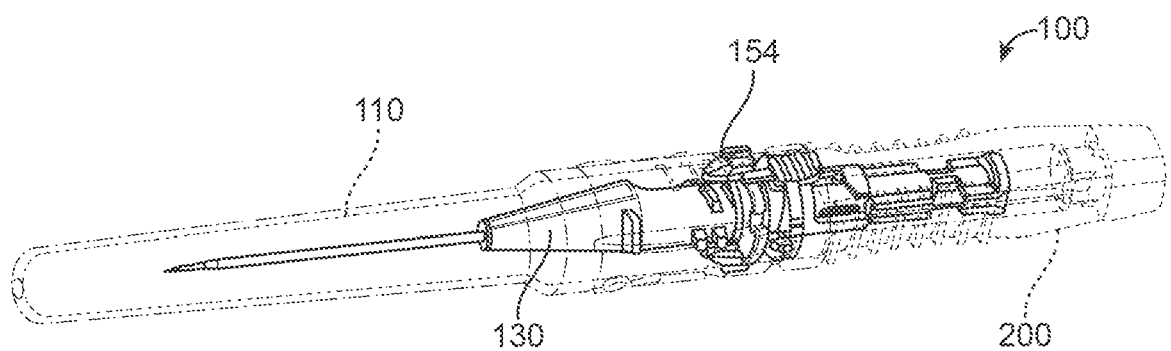
FIG. 6A illustrates a needle assembly having an optional protective cap over a catheter 130, where the catheter is positioned onto a dilator with a needle extending therethrough.

FIGS. 6A to 6E are intended to show a variation of a needle assembly 100 in an unloaded, safe, or storage position. FIG. 6A illustrates a needle assembly 100 having an optional protective cap 110 over a catheter 130, where the catheter is positioned onto a dilator with a needle extending therethrough. In those variations without a protective cap 110, the actuation of the needle assembly into a loaded or ready position can be accomplished via movement of the catheter, dilator, and/or needle.

Figure 6B:
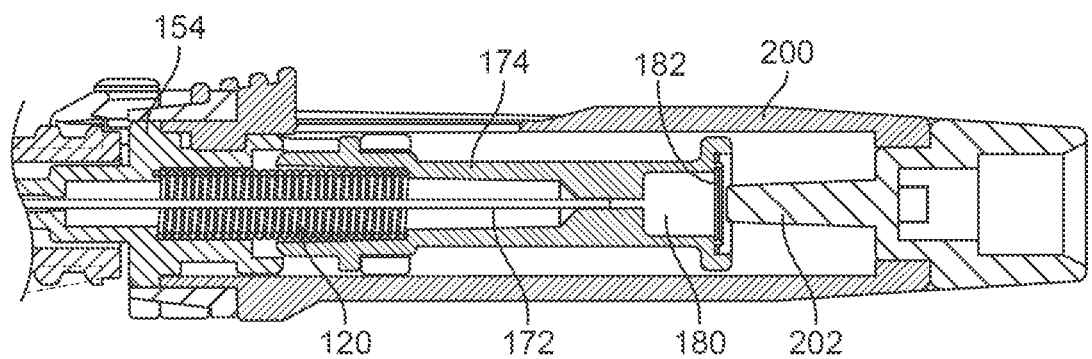
FIG. 6B illustrates a partial cross sectional view of the dilator hub, needle hub, and housing.

FIG. 6B illustrates a partial cross sectional view of the dilator hub 154, needle hub 174, and housing 200. As shown, in the unloaded configuration, the projection 202 of the housing 200 is spaced from the stop material 182. Spacing of the stop material 182 from the projection was found to improve consistency of the operation of the device assembly 100 by preventing loading of the stop material 182 by the projection or punch 202 until a medical practitioner is ready to use the device. Delaying loading of the stop material 182 prevents variability in the structural integrity of the stop material 182 due to such factors as fatigue or due to the cyclical temperature and pressure conditions that a device might experience during a sterilization process common to medical devices. In some variations, the stop material 182 can be touching the projection 202 in the unloaded configuration. However, in the unloaded configuration, the stop material 182 will not be under stress arising from the force applied by the biasing element 120. Variations of the device include configurations where the biasing element 120 applies a biasing force to the needle hub 174 in the unloaded configuration. Alternatively, other variations can include configurations where the biasing element 120 does not apply a biasing force to the needle hub 174 when in the unloaded configuration.

Figure 6C:
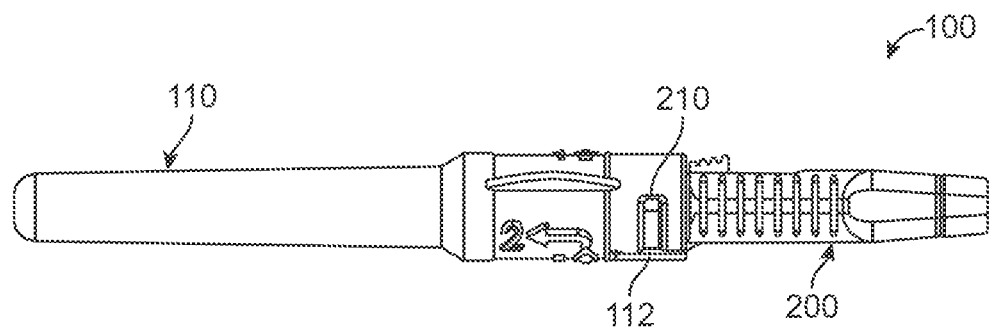
FIGS. 6C and 6D illustrate top and side views respectively of the needle assembly of FIG. 6A.
Figure 6D:
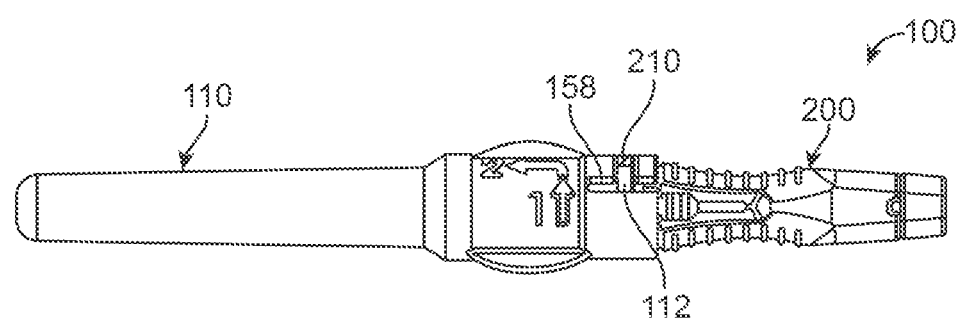

FIGS. 6C and 6D illustrate top and side views respectively of the needle assembly 100 of FIG. 6A. As shown, the cap 110 can include one or more slots/grooves 112 that mate with various portions of the needle assembly 100 to prevent inadvertent loading of the needle assembly 100. FIG. 6C shows a portion of the slot/groove 112 as accommodating an alignment feature 210 of the body 200. As shown, the alignment feature 210 bears against the slot/groove 112, which prevents movement of the cap 110 in an axial direction relative to the needle assembly 100. FIG. 6D illustrates a side view of the assembly 100 where the slot/groove 112 engages a protrusion/projection of the dilator hub 158. The assembly 100 also can include illustrated numerals (e.g., "1" and "2") along with directional indicators (e.g., "arrows"), which in the illustrated variation are on the cap 110. The numerals can provide instructions as to the sequence of operations for rotation of the cap 110. For example, the depicted indicators show that the first operation is rotation of the cap (via the "1") and removal of the cap (via the "2").

Figure 6E:
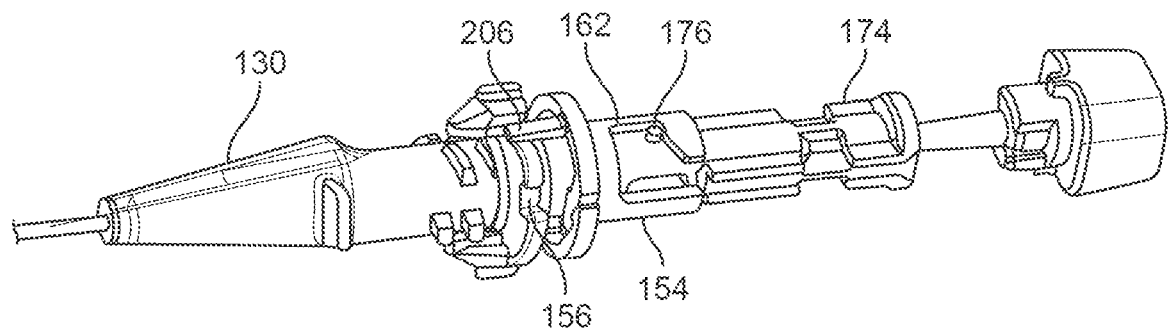
FIG. 6E illustrates the assembly of FIG. 6A with the cap and body removed to demonstrate the interaction between the dilator hub and the needle hub.

FIG. 6E illustrates the assembly of FIG. 6A with the cap 110 and body 200 removed to demonstrate the interaction between the dilator hub 154 and the needle hub 174. In the example illustrated by FIG. 6E, the biasing element (shown in FIG. 6B) urges the needle hub 174 in a proximal direction (away from the catheter 130. However, the protrusions or catch feature 176 engages a side of the slotted opening 162, which prevents the dilator from moving proximally. This engagement between the catch 176 and the slotted opening 162 allows for the spacing (or low stress state) between the stop material 182 and the punch 202 (as shown in FIG. 6B). It is also noted that when the device assembly is in the unloaded configuration, a sharp distal tip of the needle can optionally extend beyond a distal end of the catheter and/or dilator.

Figure 7A:
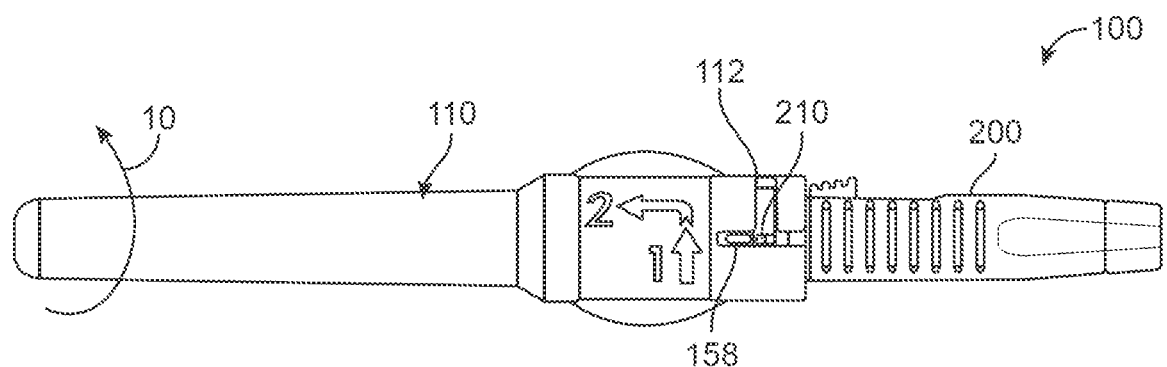
FIG. 7A shows rotation of cap in a direction to cause rotation of the dilator hub via engagement of protrusion with a slot or opening in cap.

FIGS. 7A to 7E are intended to show a variation of a needle assembly 100 actuated to a loaded or ready configuration. Again, this example shows the optional use of a cap 110 as well as other features. As shown in FIG. 7A, rotation of cap 110 in direction 10 causes rotation of the dilator hub 154 (not shown in FIG. 7A) via engagement of protrusion 158 with a slot/groove 112 in cap 110. Rotation 10 causes alignment of alignment feature 210 with protrusion 158 in the slot/groove 112 of the cap 110. This permits removal of the cap 110 from the device assembly 100. In alternate variations, the dilator hub, sheath hub, or first hub can be rotated without the use of a cap.

Figure 7B:
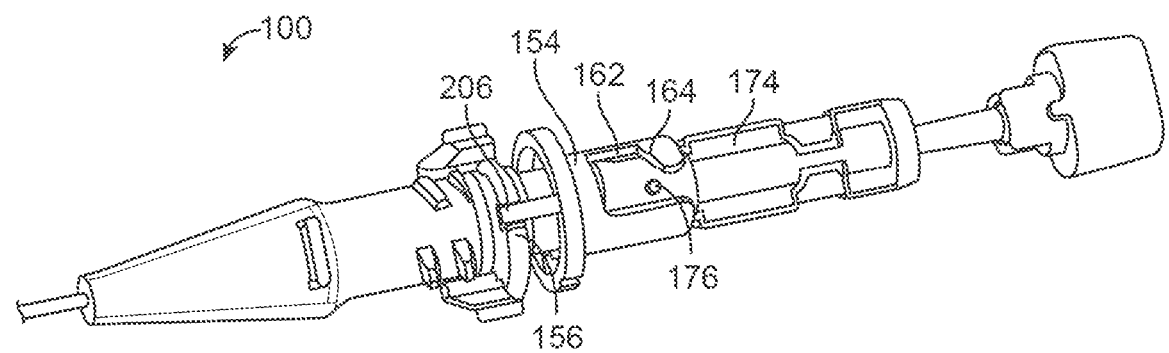
FIG. 7B illustrates the assembly of FIG. 7A with the cap removed as well as with the housing removed.
Figure 7C:
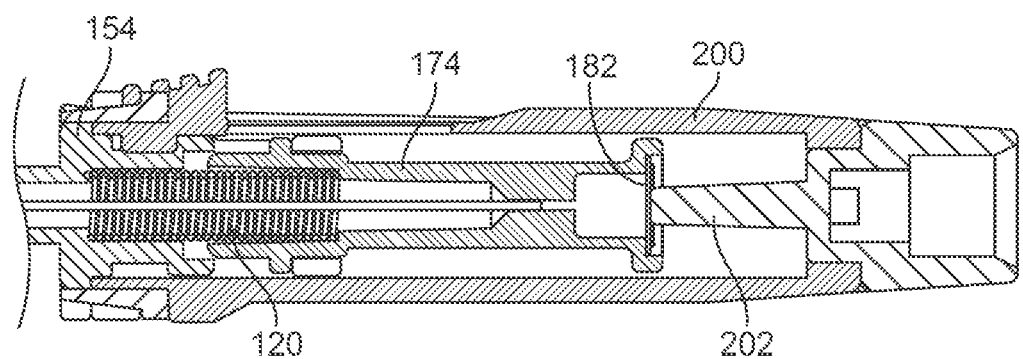
FIG. 7C illustrates a partial cross sectional view of the dilator hub, needle hub, and housing after rotation of the cap.

FIG. 7B illustrates the assembly 100 of FIG. 7A with the cap removed as well as with the housing 200 removed to illustrate the interaction of the various components. As shown, rotation of the dilator hub 154 causes locking feature 206 to engage with locking surface 156 of the dilator hub 154. This prevents further rotation (in either direction) of the dilator hub 154. Rotation of dilator hub 154 also causes the protrusion or catch feature 176 of the needle hub 174 to move along the tapered surface 164 of the slotted opening 162 in dilator hub 154 such that the protrusion or catch feature 176 no longer prevents proximal movement of the needle hub 174. FIG. 7C illustrates a partial cross sectional view of the dilator hub 154, needle hub 174, and housing 200 after rotation 10. As shown, the proximal movement of the needle hub 174 causes stop material 182 to engage the projection 202 such that the interaction between the stop material 182 and the projection 202 prevents further movement of the needle hub 174. This state represents a high stress or loaded state of the stop material 182.

Figure 7D:
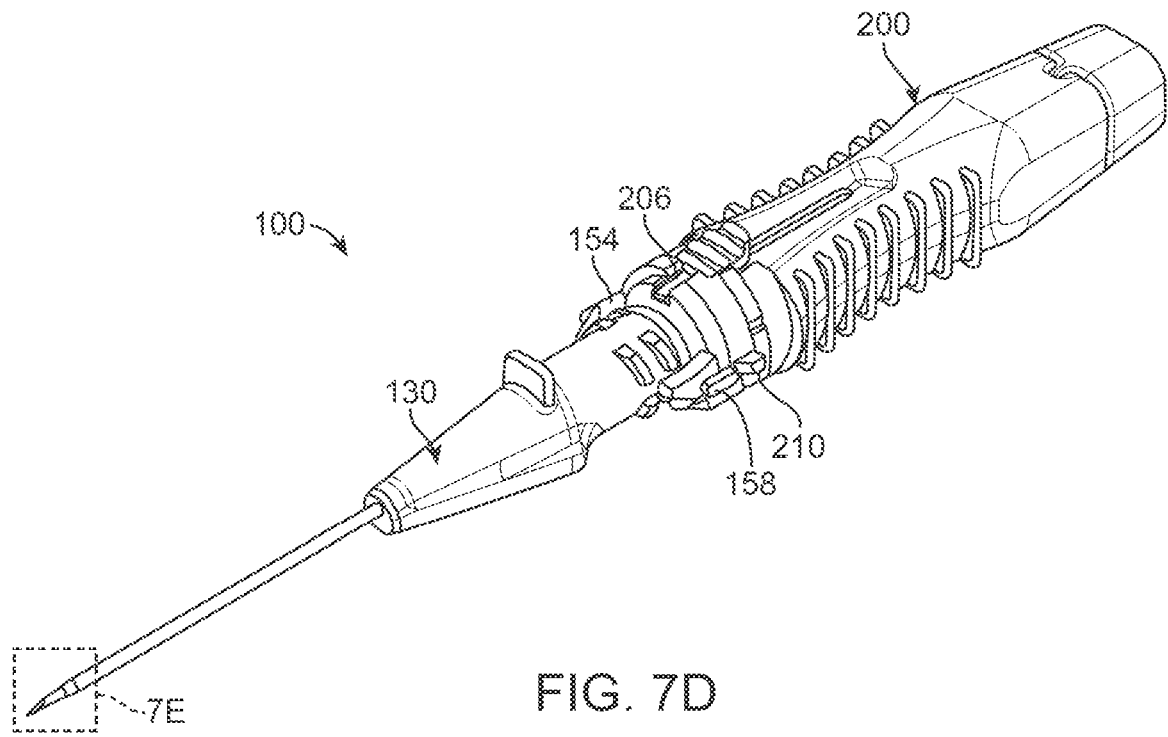
FIG. 7D illustrates a view of the device assembly after the rotation shown in FIG. 7A with the cap removed.
Figure 7E:
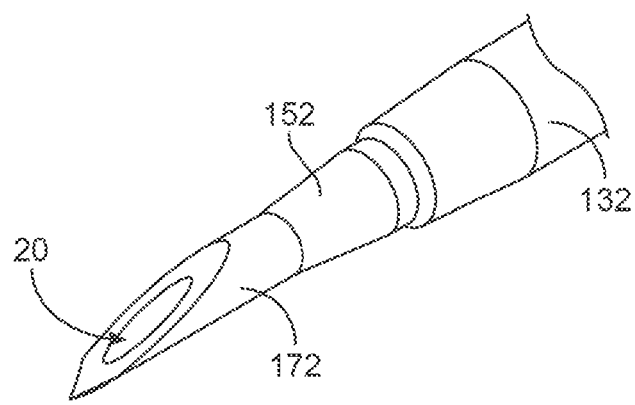
FIG. 7E illustrates a magnified view of a distal end of the device assembly of FIG. 7D.

FIG. 7D illustrates a view of the device assembly 100 after the rotation 10 shown in FIG. 7A with the cap removed. As shown, the protrusion 158 on the dilator hub 154 is aligned with the alignment feature 210 of the housing 200. In addition, the locking member 206 engages the locking surface of the dilator hub 154. FIG. 7E illustrates a magnified view of box 7E from FIG. 7D. As shown, in the ready or loaded configuration, a distal tip of the needle cannula 172 extends beyond a tip of the dilator tubing 158, which extends beyond a tip of the catheter tubing 132 allowing the device assembly 100 to be ready for use. Once inserted into a vessel blood flow 20 enters a lumen of the needle cannula 172.

Figure 8A:
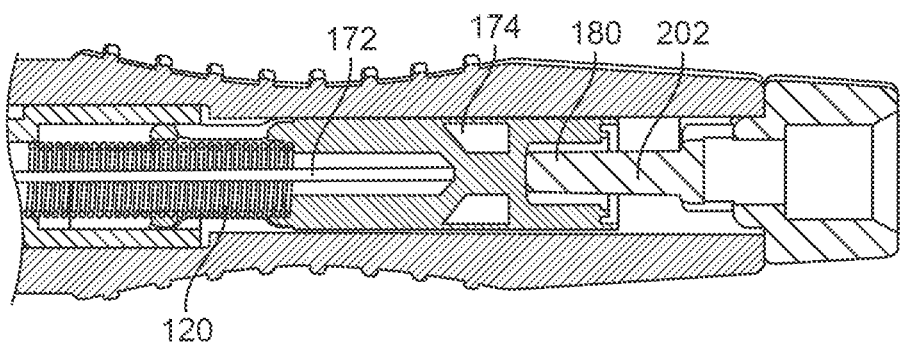
FIG. 8A shows the needle hub having moved proximally relative to the projection resulting from the biasing element driving the needle hub rearward.

As blood or other fluid flow 20 enters the needle cannula 172 it ultimately enters a chamber 180 in the dilator hub 174 that is in fluid communication with the stop material, this causes the stop material to lose structural integrity causing the needle hub 174 to move proximally relative to the projection 202 resulting from the biasing element 120 driving the needle hub 174 rearward as shown in FIG. 8A.

Figure 8B:
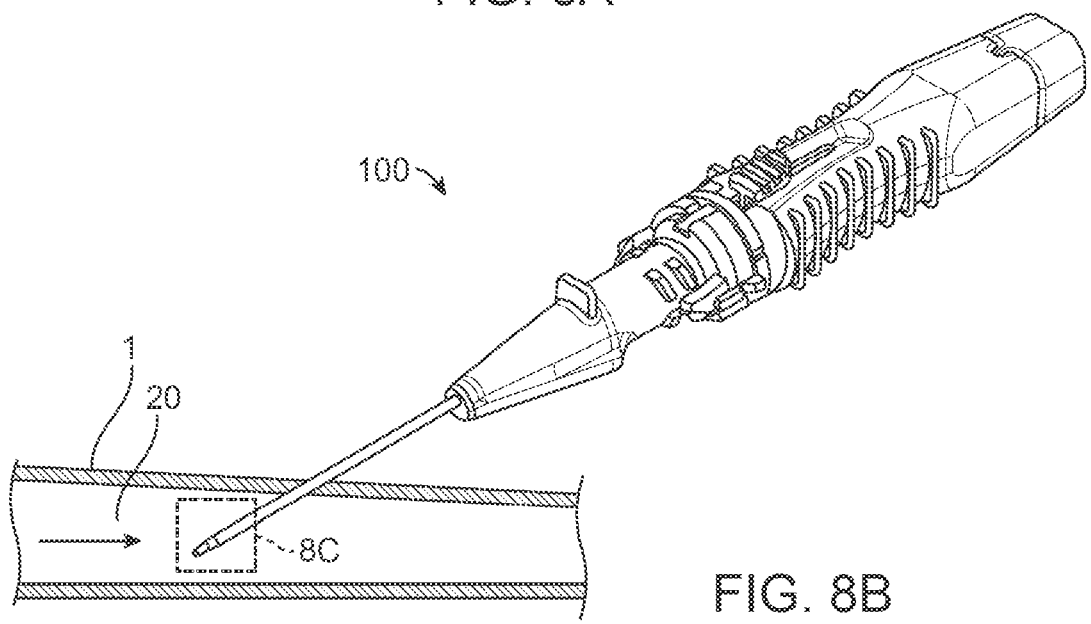
FIG. 8B illustrates a condition where a device assembly is inserted into a vessel after being activated in the loaded configuration.
Figure 8C:
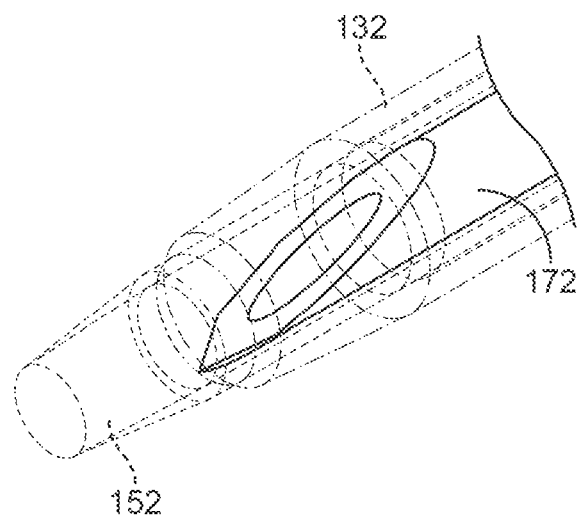
FIG. 8C illustrates a magnified view of box 8C in FIG. 8B.

FIG. 8B illustrates the condition where the device assembly is inserted into a vessel 1 after being activated in the loaded configuration. The flow of liquid 20 within the vessel 1 causes retraction of the needle hub as discussed above. FIG. 8C illustrates a magnified view of box 8C in FIG. 8B, as shown, the rearward movement of the needle hub causes the needle cannula 172 to retract within the dilator tubing 152 and/or the catheter tubing 132.

Figure 9A:
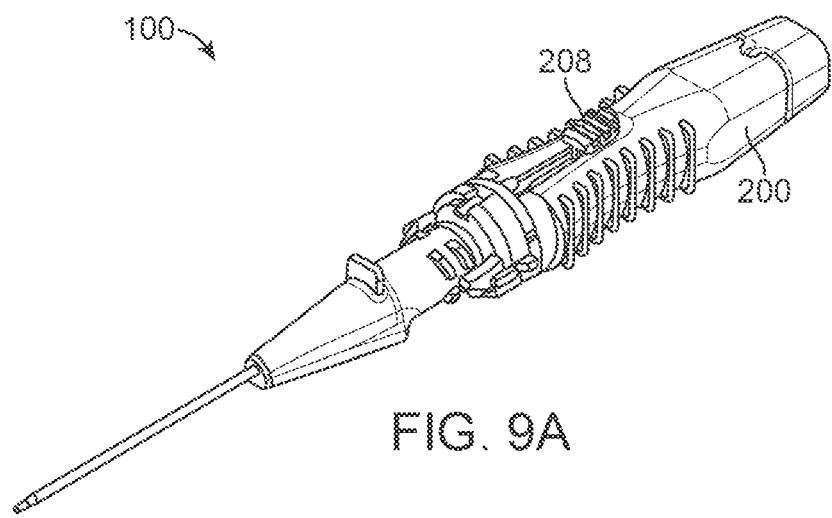
FIGS. 9A and 9B illustrate the housing with a manual retraction component.
Figure 9B:
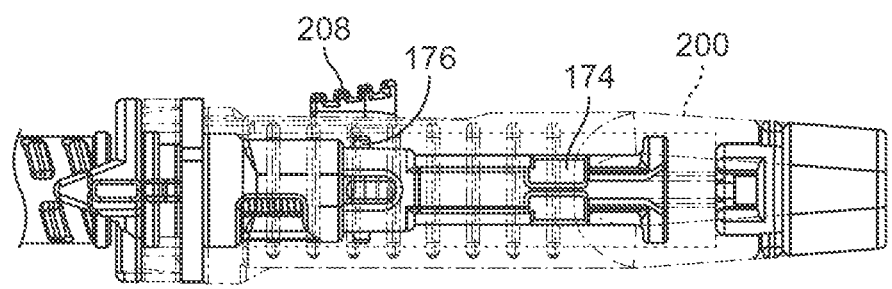
Figure 9C:
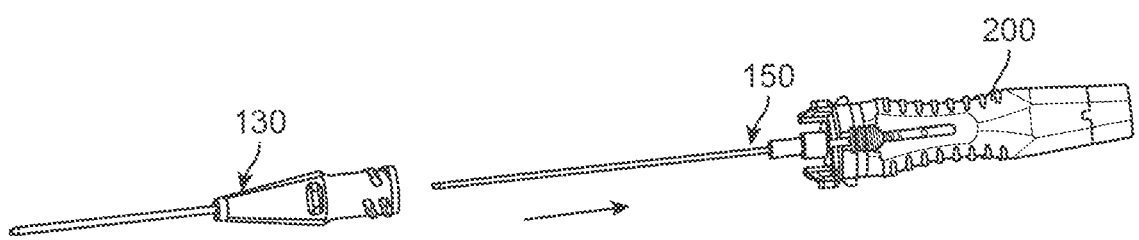
FIG. 9C illustrates removal of a dilator from a catheter 130, where the catheter remains inserted within the target vessel or area.

FIG. 9A illustrates an additional optional feature for use with the device assembly 100 described herein. In this example, the housing 200 can include a manual retraction component 208. In the illustrated variation, the retraction component comprises a sliding arm 208 that is slidable with respect to the housing 200 and, as shown in FIG. 9B, engages the protrusion or catch feature 176 of the needle hub 174. Proximal movement of the slider arm 208 causes proximal movement of the needle hub 174 to ensure that the needle tip retracts within the dilator. The operation of the slider arm 208 can serve as a confirmation that the needle is retracted or can be used as an added safety measure. Once retraction of the needle occurs or is confirmed, FIG. 9C illustrates removal of the dilator 150 from the catheter 130, which can remain inserted within the target vessel or area.

Figure 10:
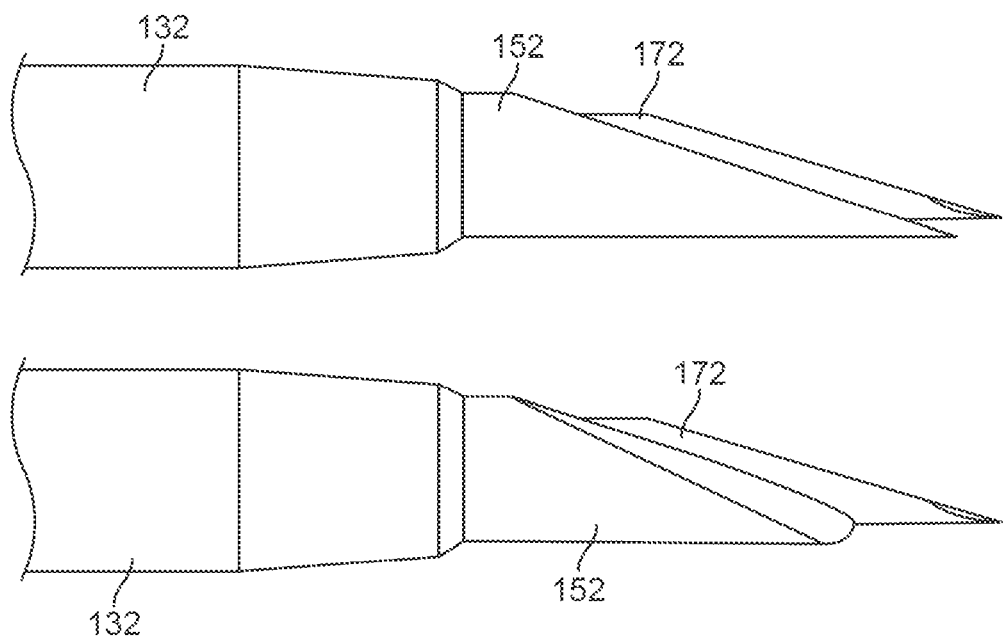
FIG. 10 illustrates a variation of a dilator with a tapered or beveled distal end to match a bevel of an accompanying needle.

FIG. 10 illustrates a variation for use with the needle assembly described herein. In this variation, the dilator 158 tip is tapered to approximate a taper of a beveled needle 172 tip. In some situations, a needle tip can penetrate the vessel cause fluid flow but prior to full insertion of the dilator tip, which might be proximally staggered from the needle tip. The tapering of the dilator as shown increases the probability that the dilator enters the penetrated vessel with the beveled needle tip. As illustrated, the dilator tip can be rounded as well as non-rounded.

Figure 11A:
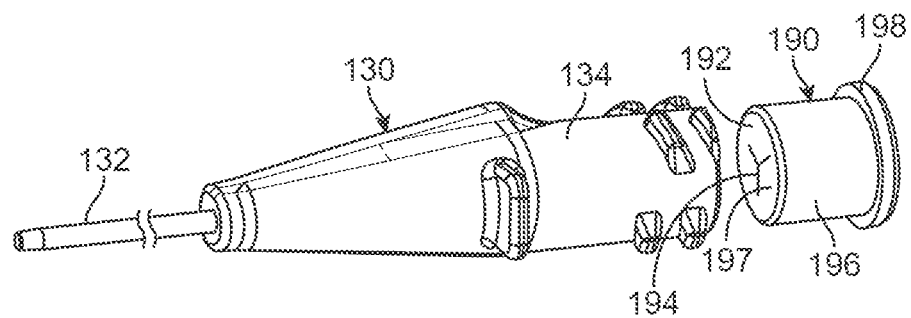
FIGS. 11A to 11C illustrate an improved valve for use with catheter.
Figure 11B:
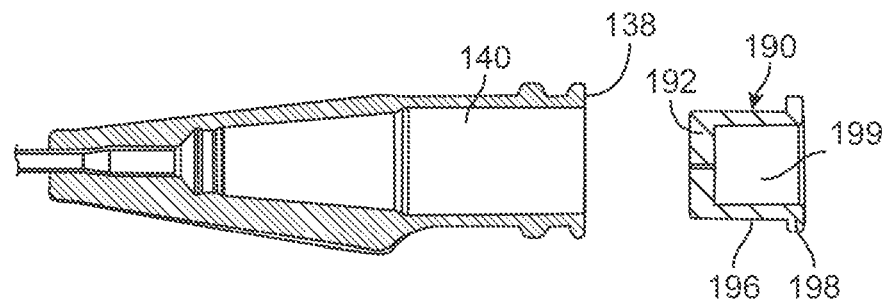
Figure 11C:
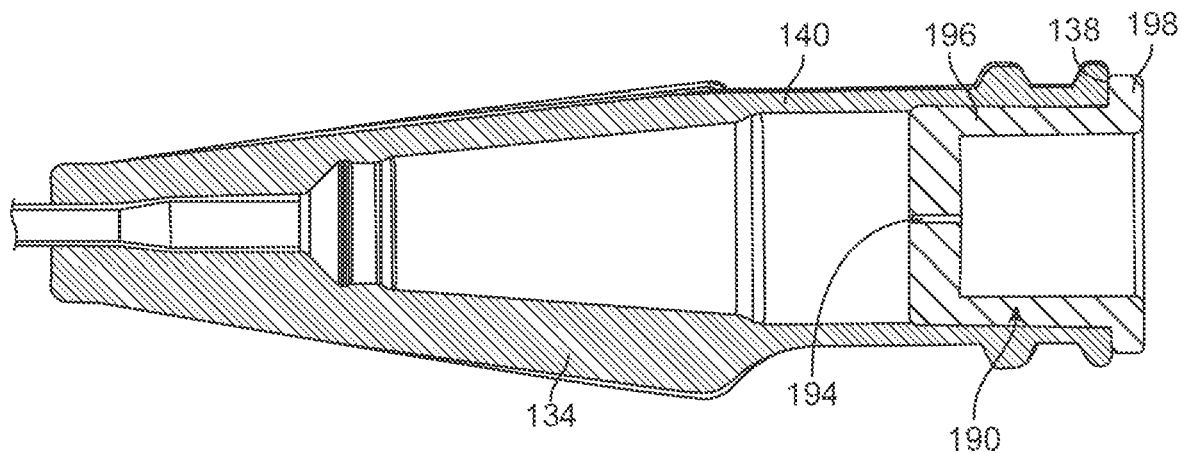

FIGS. 11A-11C illustrate an improved valve for use with catheters, including a catheter as described above. Typically, such a catheter 130 is used with a male luer (as described in FIGS. 12A-12C below). The catheter 130 includes a catheter hub 134 having a chamber 140 with a proximal surface 138 defining an open proximal end. The chamber 140 is in fluid communication with a catheter tubing 132 that is coupled the catheter. The tubing includes one or more lumens in fluid communication with the chamber 140. The valve or septum valve 190 includes a barrier layer (or septum) 192 at a distal end. the barrier layer 192 can have one or more slits 194. The illustrated variation shows a barrier layer 192 with 3 slits 194 that form three leaflet structures 197 or flaps. However, variations of the valve 190 include any number of slits forming any number of leaflets. The barrier layer 192 generally includes a flexible or semi-flexible material that is compatible with exposure to blood, medicaments, and other fluids commonly encountered during catheterization/infusion procedures.

As shown in FIG. 11B, the valve includes a wall portion 196 extending proximally from the barrier layer 192 and defines a valve cavity 199. A flange portion 198 is formed around the wall 196 at a near/proximal end of the valve 190. The flange portion comprises a diameter greater than a diameter of the wall portion. Variations of the valve 190 include a flange portion 198 that encircles the valve 190. Alternatively, the flange portion 198 can include openings or segments such that it is not circumferentially continuous about the wall.

FIG. 11C shows the valve 190 coupled to the catheter hub 134 such that the flange portion 198 engages the proximal surface 138 of the catheter hub 134 and is exterior to the chamber 140 of the hub 134. The wall portion 196 of the valve 190 engages a surface of the chamber. The valve 190 can be affixed to the catheter at various points. For example, variations of the assembly include a valve 190 that is only affixed to the catheter hub 134 at the flange portion 198 using an adhesive or joining material where the wall portion 196 is simply positioned against a wall of the chamber 140. Alternatively, or in combination, the valve 190 can be affixed to the catheter hub 134 at the exterior wall portion 196. In an alternate variation, the valve 190 can simply be press-fit into the catheter hub 134. Any number of features known to those in the art can be used to facilitate seating of the valve 190 within the catheter hub 134 (e.g., pockets, ribs, increased frictional resistance of the surface of the valve or chamber, etc.)

Figure 12A:
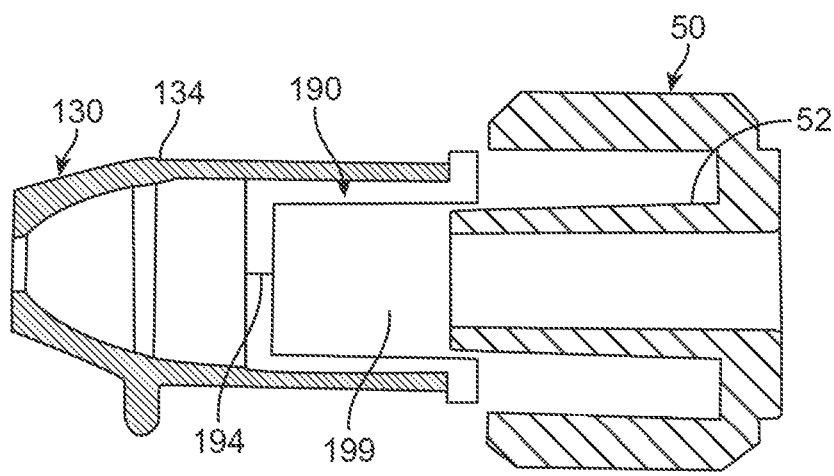
FIGS. 12A to 12C show a luer fitting inserted into the catheter valve assembly of FIG. 11C.
Figure 12B:
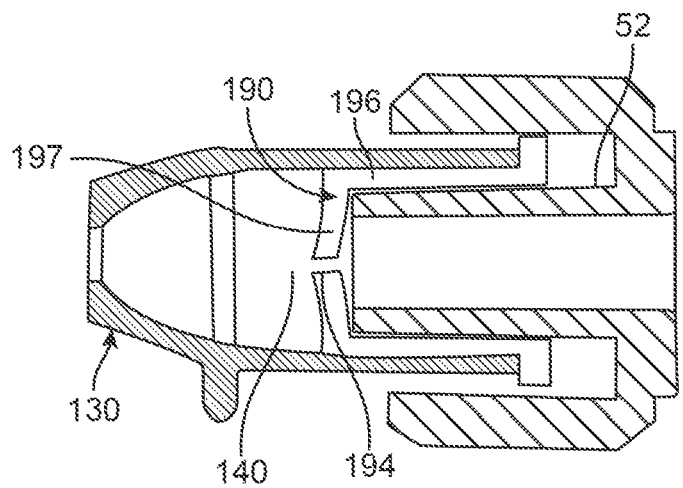
Figure 12C:
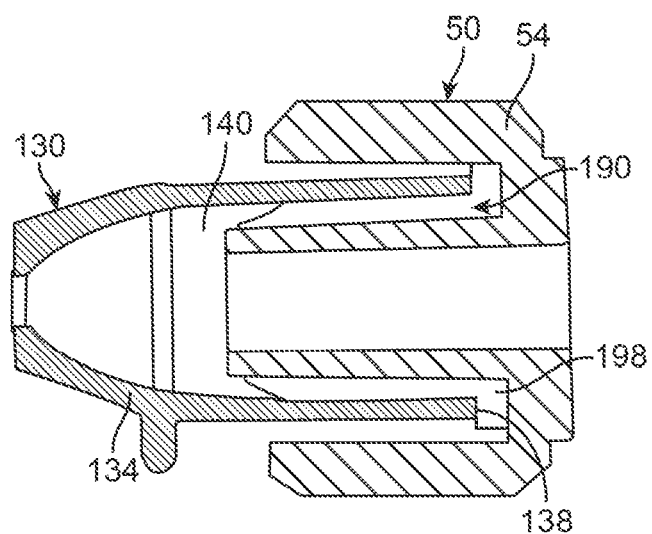

FIGS. 12A-12C show a cross sectional view of a catheter valve assembly 130 to demonstrate an example of a luer fitting 50 being inserted into the valve 190 of the catheter assembly 130. The figures do not show male or female threading on either the luer fitting 50 or catheter hub 134 for purposes of clarity in showing the interaction between a male luer 52 of the luer fitting 50 and the catheter 130.

FIG. 12A illustrates insertion of a male luer 52 having a taper into the cavity of the valve 190. As shown in FIG. 12B, as the surface of the male luer 52 engages the wall portion 196, the wall portion 196 is compressed against a surface of the catheter chamber 140. As the male luer 52 advances, the slit 194 of the valve 190 opens in a distal direction. Ultimately, as shown in FIG. 12C, insertion of the male luer 52 into the cavity of the valve 190 causes the distal end of the male luer 52 to open the slit, while the lateral surface of the male luer 52 engages the wall portion 196 of the valve 190 causing the wall portion 196 to engage an interior surface of the chamber 140. The connector portion 54 of the luer fitting 50 engages the flange portion 198 against the proximal surface 138 of the catheter hub 134. Removal of the luer fitting 50 from the catheter hub 134 causes the leaflets 197 of the valve formed by the slit to return to a closed configuration.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

The invention claimed is:

1. A catheter assembly for use with a male luer having a distal end and a lateral surface, the male luer having a connector portion, the catheter assembly comprising:
    a catheter hub having a chamber and having a proximal-most surface defining an open proximal end;
    a catheter tubing coupled the catheter hub and having a lumen in fluid communication with the chamber;
    a septum valve comprising:
        a barrier layer at a far end of the septum valve;
        a wall portion extending proximally from the barrier layer towards a near end of the septum valve, the wall portion defining a valve cavity therein, the barrier layer extending perpendicularly to the wall portion at the far end, at least one slit extending through the barrier layer forming a plurality of leaflets in the barrier layer;
        a flange portion at the near end of the septum valve, the flange portion having a diameter greater than a diameter of the wall portion, and where the valve cavity has an open proximal end;
    the septum valve is coupled to the catheter hub such that the flange portion engages the proximal-most surface of the catheter hub exterior to the chamber and the wall portion engages a surface of the chamber; and
    wherein insertion of the male luer into the open proximal end of the valve cavity causes the distal end of the male luer to open the at least one slit and separate the plurality of leaflets, while the lateral surface of the male luer engages the wall portion at an interior of the valve cavity causing the wall portion to engage the surface of the chamber, and where the connector portion directly engages the flange portion against the proximal-most surface of the catheter hub.

2. The catheter assembly of claim 1, wherein the flange portion of the septum valve is affixed to the proximal-most surface of the catheter hub and where the wall portion of the septum valve contacts the surface of the chamber of the catheter hub.

3. The catheter assembly of claim 1, wherein a perimeter of the at least one slit is limited to the barrier layer such that the leaflets do not extend into the wall portion.

4. The catheter assembly of claim 1, wherein the at least one slit is branched such that the plurality of leaflets comprises at least three leaflets.

5. The catheter assembly of claim 1, wherein an entire outer surface of the wall portion contacts the surface of the chamber.

6. The catheter assembly of claim 1, wherein an entire outer surface of the wall portion comprises a cylindrical shape having a uniform outer diameter.

7. The catheter assembly of claim 1, wherein a thickness of each of the plurality of leaflets is the same.

8. The catheter assembly of claim 7, wherein the plurality of leaflets are located at the far end of the septum valve such that separation of the plurality of leaflets caused by insertion of the male luer causes the plurality of leaflets to deform out of the valve cavity.

9. The catheter assembly of claim 1, wherein the septum valve is located within the chamber.

10. The catheter assembly of claim 9, wherein a length of the chamber is greater than a length of the septum valve.

* * * * *